US00PP17524P2

(12) United States Plant Patent
van den Top

(10) Patent No.: US PP17,524 P2
(45) Date of Patent: Mar. 27, 2007

(54) *HOSTA* PLANT NAMED 'MAGIC FIRE'

(50) Latin Name: *Hosta fluctuans*
Varietal Denomination: Magic Fire

(76) Inventor: Hendrik Jan van den Top, Wesselweg 46, 3771 PC, Barneveld (NL)

( * ) Notice: Subject to any disclaimer, the term of this patent is extended or adjusted under 35 U.S.C. 154(b) by 0 days.

(21) Appl. No.: 11/204,330

(22) Filed: Aug. 15, 2005

(51) Int. Cl.
*A01H 5/00* (2006.01)

(52) U.S. Cl. ..... Plt./353

(58) Field of Classification Search ..... Plt./353
See application file for complete search history.

*Primary Examiner*—Kent Bell
(74) *Attorney, Agent, or Firm*—C. A. Whealy

(57) ABSTRACT

A new and distinct cultivar of *Hosta* plant named 'Magic Fire', characterized by its relatively compact plant habit; green and pale yellow variegated leaf color; and light lavender-colored flowers that are positioned above the foliage on strong and erect scapes.

1 Drawing Sheet

Botanical designation: *Hosta fluctuans.*
Cultivar denomination: 'Magic Fire'.

BACKGROUND OF THE INVENTION

The present Invention relates to a new and distinct cultivar of *Hosta* plant, botanically known as *Hosta fluctuans,* and hereinafter referred to by the cultivar name Magic Fire.

The new *Hosta* was discovered by the Inventor in a controlled environment in Barneveld, The Netherlands, as a whole plant mutation of the *Hosta fluctuans* cultivar Sagae, not patented, in June, 1998.

Asexual reproduction of the new cultivar by divisions and by tissue-cultured microplants in a controlled environment in Barneveld, The Netherlands since January, 2004, has shown that the unique features of this new *Hosta* are stable and reproduced true to type in successive generations.

SUMMARY OF THE INVENTION

Plants of the cultivar Magic Fire have not been observed under all possible environmental and cultural conditions. The phenotype may vary somewhat with variations in environment such as temperature and light intensity without, however, any variance in genotype.

The following traits have been repeatedly observed and are determined to be the unique characteristics of 'Magic Fire'. These characteristics in combination distinguish 'Magic Fire' as a new and distinct *Hosta* cultivar:

1. Relatively compact plant habit.
2. Green and pale yellow variegated leaf color.
3. Light lavender-colored flowers that are positioned above the foliage on strong scapes.

Plants of the new *Hosta* can be compared to plants of the parent, the cultivar Sagae. In side-by-side comparisons conducted in Barneveld, The Netherlands, plants of the new *Hosta* differed from plants of the cultivar Sagae in the following characteristics:

1. Leaves of plants of the new *Hosta* were more cordate than leaves of plants of the cultivar Sagae.
2. Leaves of plants of the new *Hosta* had broad pale yellow-colored margins whereas leaves of plants of the cultivar Sagae had very narrow pale yellow-colored margins.
3. Leaves of plants of the new *Hosta* had eight vein pairs whereas leaves of plants of the cultivar Sagae had seven vein pairs.

Plants of the new *Hosta* can also be compared to plants of the cultivar Liberty, disclosed in U.S. Plant Pat. No. 12,531. In side-by-side comparisons conducted in Barneveld, The Netherlands, plants of the new *Hosta* differed from plants of the cultivar Liberty in the following characteristics:

1. Leaves of plants of the new *Hosta* were much smaller than leaves of plants of the cultivar Liberty.
2. Leaves of plants of the new *Hosta* had eight vein pairs whereas leaves of plants of the cultivar Liberty had twelve vein pairs.

BRIEF DESCRIPTION OF THE PHOTOGRAPHS

The accompanying colored photographs illustrate the overall appearance of the new *Hosta,* showing the colors as true as it is reasonably possible to obtain in colored reproductions of this type. Colors in the photographs may differ slightly from the color values cited in the detailed botanical description which accurately describe the actual colors of the new *Hosta.*

The photograph at the top of the sheet comprises a side perspective view of a typical flowering plant of 'Magic Fire' grown in a container.

The photograph at the bottom of the sheet is a close-up view of typical flowers and a typical leaf of 'Magic Fire'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and the following description were about two years old and grown in 17-cm containers in a glass-covered greenhouse and under conditions which closely approximate commercial production conditions during the spring in Barneveld, The Netherlands. During the production of the plants, day temperatures were about 20° C. and night temperatures were about 16° C.

Botanical Classification: *Hosta fluctuans* cultivar Magic Fire.

Parentage: Whole plant mutation of *Hosta fluctuans* cultivar Sagae, not patented.

Propagation:

*Propagation method.*—By tissue culture.

*Rooting time.*—Tissue-cultured microplants will initiate roots in about six weeks.

*Root description.*—Fleshy.

Plant description:

*Form.*—Perennial flowering plant; initially upright becoming outwardly arching as leaves develop; inverted triangle, mounded. Moderate to freely clumping. Moderately vigorous to vigorous growth habit.

*Plant height to top of leaf plane.*—About 26 cm.

*Plant height to top of flowers.*—About 45 cm.

*Plant diameter.*—About 55 cm.

*Foliage description.*—Arrangement: Basal, simple, generally symmetrical. Length: About 13 to 17 cm. Width: About 11 to 13 cm. Shape: Cordate. Apex: Cuspidate. Base: Cordate. Margin: Entire; slightly undulate. Texture, upper and lower surfaces: Smooth, glabrous; leathery; veins sunken on upper surface, prominent on lower surface. Venation: Pinnate, arcuate; eight vein pairs per leaf. Petiole: Length: About 13 to 16 cm. Diameter: About 7 to 10 mm. Texture, upper and lower surfaces: Smooth, glabrous. Color: Developing foliage, upper surface: Center, 146B; towards the margins, irregular sectors, 10B. Developing foliage, lower surface: Center, N138C; towards the margins, irregular sectors, 10D. Fully developed foliage, upper surface: Center, close to 137C; towards the margins, irregular sectors, 11C, and irregular stripes, 144A to 144B. Fully developed foliage, lower surface: Center, close to 191A; towards the margins, irregular sectors, 11C. Petiole color: Upper surface, 139D; lower surface, 145C; margin, 145C.

Flower description:

*Appearance.*—Single campanulate flowers with fused perianth arranged on racemes. Flowering stems arise from leaf axils. Typically about two flowering stems per plant. Flowers not persistent. Flowers not fragrant.

*Natural flowering season.*—Summer in the Netherlands; flowering recurrent during this period.

*Flower longevity.*—About one week.

*Inflorescence height.*—About 12 to 16 cm.

*Inflorescence diameter.*—About 7 to 9 cm.

*Flower length.*—About 5 cm.

*Flower diameter.*—About 2 cm.

*Flower buds.*—Length: About 1.5 cm. Diameter: About 5 mm. Shape: Ovoid. Color: Close to 91D.

*Perianth.*—Arrangement: Three interior and three exterior tepals; fused. Tepal length: About 5 cm. Tepal width: About 1 cm. Tepal shape: Elongated; apex, apiculate; margin, entire. Tepal texture, upper and lower surfaces: Smooth; glabrous; satiny. Tepal color: When opening and fully opened, upper surface: 85D; towards the center, About 85A to 85C. When opening and fully opened, lower surface: 85D.

*Floral bracts.*—Arrangement: One per flower at pedicel base. Length: About 1 cm. Width: About 5 mm. Shape: Broadly lanceolate. Apex: Acute. Margin: Entire. Color, upper and lower surfaces: Towards the base, N155D; towards the apex, 160A to 160B.

*Scape.*—Length: About 45 cm. Diameter: About 6 to 8 mm. Aspect: Slightly bent. Strength: Strong, flexible. Texture: Smooth; glabrous. Color: 146D.

*Pedicel.*—Length: About 5 mm. Diameter: About 2 mm. Aspect: Bent. Strength: Moderately strong. Texture: Smooth, glabrous. Color: Close to 146D.

*Reproductive organs.*—Stamens: Quantity: About six per flower. Stamen length: About 4.5 cm. Stamen color: Towards the base, 145C; towards the apex, 155C. Anther length: About 5 mm. Anther color: 165B; stripes, 165A. Pollen color: 13A. Pistils: Quantity: One per flower. Style length: About 5 cm. Style color: 145C to 145D. Stigma color: 85B.

*Seed/fruit description.*—Seed and fruit development have not been observed.

Disease/pest resistance: Plants of the new *Hosta* have not been noted to be resistant to pathogens and pests common to *Hosta*.

Temperature tolerance: Plants of the new *Hosta* have been observed to tolerate temperatures from −30° to 50° C.

It is claimed:

1. A new and distinct cultivar of *Hosta* plant named 'Magic Fire', as illustrated and described.

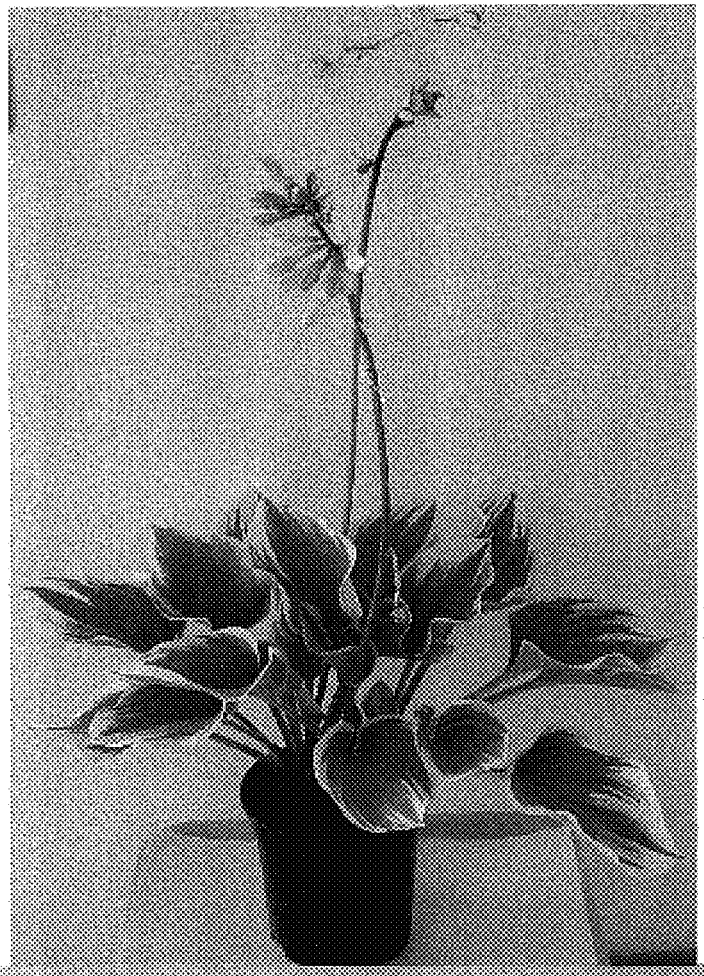
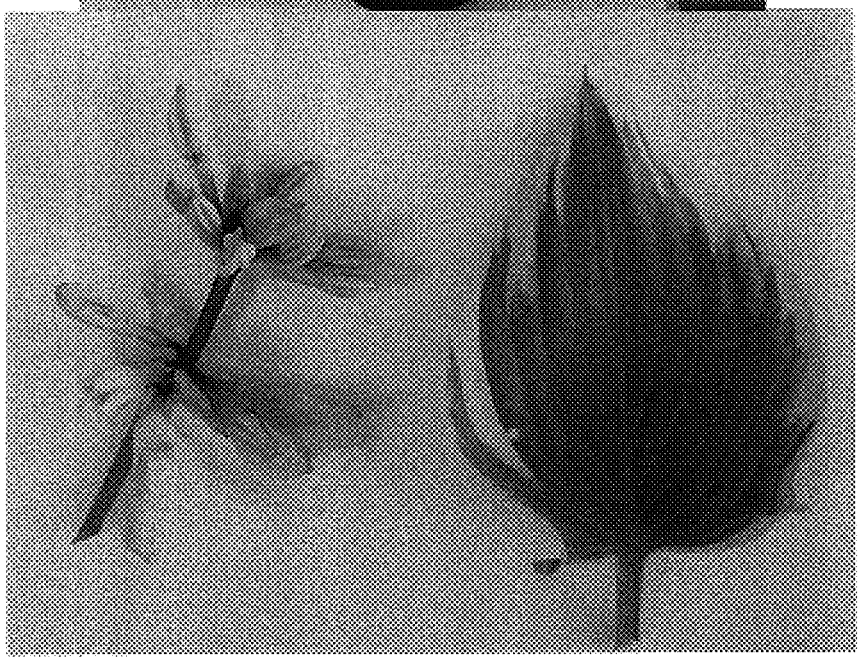

* * * * *